United States Patent
Parker et al.

(10) Patent No.: US 12,156,742 B2
(45) Date of Patent: Dec. 3, 2024

(54) HEARING DEVICE-BASED SYSTEMS AND METHODS FOR DETERMINING A QUALITY INDEX FOR A CARDIORESPIRATORY MEASUREMENT

(71) Applicant: SONOVA AG, Staefa (CH)

(72) Inventors: Anna M. Parker, Basel (CH); Nina Stumpf, Maennedorf (CH); Niklas Ignasiak, Zürich (CH); Nicholas Ohs, Zürich (CH); Manuela Feilner, Egg b. Zürich (CH); Hans-Ueli Roeck, Hombrechtikon (CH); Nadim El Guindi, Zürich (CH)

(73) Assignee: Sonova AG, Staefa (CH)

( * ) Notice: Subject to any disclaimer, the term of this patent is extended or adjusted under 35 U.S.C. 154(b) by 438 days.

(21) Appl. No.: 17/585,373

(22) Filed: Jan. 26, 2022

(65) Prior Publication Data
US 2023/0233149 A1    Jul. 27, 2023

(51) Int. Cl.
| A61B 5/00 | (2006.01) |
| A61B 5/021 | (2006.01) |
| A61B 5/024 | (2006.01) |
| A61B 5/026 | (2006.01) |
| A61B 5/08 | (2006.01) |
| A61B 5/113 | (2006.01) |
| A61B 5/145 | (2006.01) |

(52) U.S. Cl.
CPC ............ *A61B 5/6815* (2013.01); *A61B 5/021* (2013.01); *A61B 5/02405* (2013.01); *A61B 5/026* (2013.01); *A61B 5/0816* (2013.01); *A61B 5/113* (2013.01); *A61B 5/14542* (2013.01); *A61B 5/7221* (2013.01); *A61B 5/742* (2013.01); *A61B 2562/0219* (2013.01)

(58) Field of Classification Search
CPC .......... A61B 2562/0219; A61B 5/0205; A61B 5/021; A61B 5/02405; A61B 5/02416; A61B 5/02438; A61B 5/026; A61B 5/0816; A61B 5/1118; A61B 5/113; A61B 5/14542; A61B 5/14551; A61B 5/6803; A61B 5/6815; A61B 5/6817; A61B 5/7221; A61B 5/7264; A61B 5/7275; A61B 5/742; H04R 1/1041; H04R 2225/61

See application file for complete search history.

(56) References Cited

U.S. PATENT DOCUMENTS 9,788,785 B2    10/2017    Leboeuf
11,109,809 B2    9/2021    Leboeuf
(Continued)

FOREIGN PATENT DOCUMENTS

CN    103976723    8/2014

*Primary Examiner* — Kile O Blair
(74) *Attorney, Agent, or Firm* — ALG Intellectual Property, LLC

(57) ABSTRACT

An illustrative hearing system may be configured to receive, from an inertial sensor included in a hearing device configured to be worn by a user, inertial sensor data representative of at least one of motion of the hearing device or orientation of the hearing device. The hearing system may further be configured to determine, based on the inertial sensor data, an activity state of the user and to determine, based on the activity state, a cardiorespiratory quality index representative of a quality level of a measurement of a cardiorespiratory property of the user.

21 Claims, 6 Drawing Sheets

(56) References Cited

U.S. PATENT DOCUMENTS

2016/0094899 A1* 3/2016 Aumer ................ A61B 5/6802
                                                    340/870.07
2021/0289298 A1    9/2021 Roeck

* cited by examiner

HEARING DEVICE-BASED SYSTEMS AND METHODS FOR DETERMINING A QUALITY INDEX FOR A CARDIORESPIRATORY MEASUREMENT

BACKGROUND INFORMATION

A hearing device may enable or enhance hearing by a user wearing the hearing device by providing audio content received by the hearing device to the user. For example, a hearing aid may provide an amplified version of the audio content to the user to enhance hearing by the user. As another example, a sound processor included in a cochlear implant system may provide electrical stimulation representative of the audio content to the user to enable hearing by the user.

In some cases, it may be desirable for a hearing device to be configured to detect motion and/or orientation of a user wearing the hearing device. For example, motion of the user wearing the hearing device may, in some instances, affect the accuracy of a measurement for a condition (e.g., blood pressure or another cardiorespiratory property) of the user that may be generated by the hearing device and/or a separate device worn by the user. To this end, it may be desirable for a hearing device to include an inertial sensor configured to detect a motion and/or an orientation of the hearing device while the hearing device is worn by the user. Such detected motion and/or orientation may be used to determine a quality level for a measurement of a user condition generated by the hearing device and/or a separate device worn by the user.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
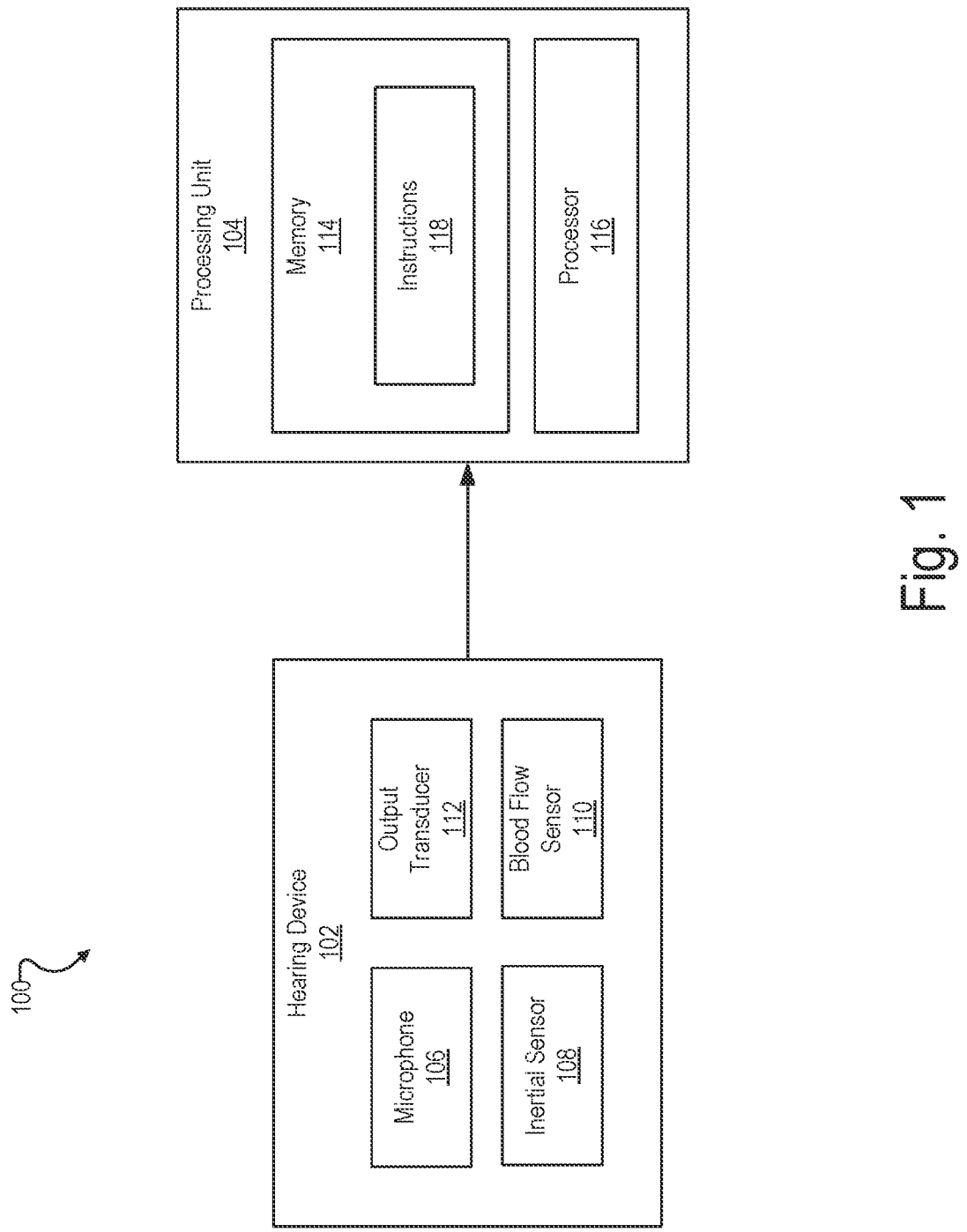
FIG. 1 shows an illustrative implementation of a hearing system.

An illustrative hearing system may be configured to determine a cardiorespiratory quality index representative of a quality level of a measurement of a cardiorespiratory property of the user based on inertial sensor data received from an inertial sensor included in a hearing device configured to be worn by a user.

For example, the hearing system may be configured to receive, from an inertial sensor included in a hearing device configured to be worn by a user, inertial sensor data representative of at least one of a motion of the hearing device or an orientation of the hearing device, determine, based on the inertial sensor data, an activity state (e.g., a level of stress, an intensity or type of an activity, or a posture) of the user, and determine, based on the activity state, a cardiorespiratory quality index representative of a quality level of a measurement of a cardiorespiratory property (e.g., a blood pressure, a respiratory rate, a heart rate variability, a blood analyte level, or a capillary oxygen saturation) of the user. The hearing system may further be configured to display the cardiorespiratory quality index to the user or to transmit and/or output the cardiorespiratory quality index to a display device (e.g. a wearable device such as a smartphone, a tablet, a smartwatch, or the like) configured to provide a display of the cardiorespiratory quality index to the user.

The principles described herein may result in improved hearing systems compared to conventional systems that are not configured to determine a cardiorespiratory quality index based on an activity state of the user, as well as provide other benefits as described herein. For example, a hearing system configured to determine a cardiorespiratory quality index based on an activity state of the user may help determine whether a fluctuation in a measurement of the cardiorespiratory property is due to a change in the activity state, a low quality of the measurement, and/or an underlying health condition of the user. Moreover, a hearing system configured to determine a cardiorespiratory quality index based on an activity state of the user may allow the hearing system to be more computationally efficient and/or more conservative with available resources (e.g., processing power and/or battery power) and/or more reliable and/or accurate with regard to measuring the cardiorespiratory property by adjusting one or more settings of the hearing system and/or performing other operations. For example, the hearing system may abstain from taking a measurement of the cardiorespiratory property and/or interrupt the measurement and/ or invalidate at least part of measurement data obtained from the measurement and/or change a configuration of a blood flow sensor and/or an electrocardiogram sensor in contact with the user and/or disable a blood flow sensor and/or an electrocardiogram sensor in contact with the user. As another example, the hearing system may take a measurement of the cardiorespiratory property and/or enable a blood flow sensor and/or an electrocardiogram sensor in contact with the user and/or initiate a recording of data generated by a blood flow sensor and/or an electrocardiogram sensor in contact with the user.

For example, the cardiorespiratory quality index may be provided as any value between a predefined minimum value and a predefined maximum value, which is representative of a probable quality level of a measurement of the cardiorespiratory property as it can be estimated based on the activity state. E.g., a cardiorespiratory quality index corresponding to the predefined minimum value may indicate a minimum probability, and a quality index corresponding to the predefined maximum value may indicate a maximum probability of a highest level of quality of a measurement of the cardiorespiratory property. The cardiorespiratory property may be a property related to the respiratory system of the user (e.g., a respiration rate) and/or a cardiovascular property (e.g., a blood pressure, a heart rate variability, a blood analyte level, or a capillary oxygen saturation (SpO2)). To illustrate, e.g., when the cardiorespiratory property is selected as a blood pressure of the user, the cardiorespiratory quality index may be a blood pressure quality index representative of a blood pressure measurement of the user. The blood pressure quality index, as it can be estimated based on the activity state (e.g., a posture of the user, a level of stress, an intensity and/or type of an activity performed by the user, and/or change thereof) may then help the user to determine an origin of a fluctuation of the blood pressure measurement and/or may allow the hearing system to perform an operation depending on the blood pressure quality index, e.g., abstaining from taking a blood pressure measurement or taking a blood pressure measurement and/or disabling or enabling a blood flow sensor and/or an electrocardiogram sensor in contact with the user and/or changing a configuration thereof and/or initiating a recording of data generated by a blood flow sensor and/or an electrocardiogram sensor.

Various embodiments will now be described in more detail with reference to the figures. The systems, hearing devices, and methods described herein may provide one or more of the benefits mentioned above and/or various additional and/or alternative benefits that will be made apparent herein. While embodiments for a hearing system configured to determine a cardiorespiratory quality index are described below, the described embodiments may further be configured to determine a quality level for other measurements of user conditions that may be affected by motion and/or body orientation of the user (e.g., body temperature).

FIG. 1 shows an illustrative implementation 100 of a hearing system configured to determine a cardiorespiratory quality index representative of a quality level of a measurement of a cardiorespiratory property of the user based on inertial sensor data received from an inertial sensor included in a hearing device configured to be worn by a user. As shown, implementation 100 includes a hearing device 102 communicatively coupled with a processing unit 104. Implementation 100 may include additional or alternative components as may serve a particular implementation.

Hearing device 102 may be implemented by any type of hearing device configured to enable or enhance hearing by a user wearing hearing device 102. For example, hearing device 102 may be implemented by a hearing aid configured to provide an amplified version of audio content to a user, a sound processor included in a cochlear implant system configured to provide electrical stimulation representative of audio content to a user, a sound processor included in a bimodal hearing system configured to provide both amplification and electrical stimulation representative of audio content to a user, or any other suitable hearing prosthesis.

As shown, hearing device 102 includes a microphone 106, an inertial sensor 108, a blood flow sensor 110, and an output transducer 112. Hearing device 102 may include additional or alternative components as may serve a particular implementation. E.g., an electrocardiogram (ECG) sensor may be provided in place of or in addition to blood flow sensor 110. Other components may comprise, e.g., at least one of a battery, a power management, a computer processing device, a memory, a communication interface (e.g., a Bluetooth radio), and a user interface (e.g., a push button) to control the hearing device 102.

Microphone 106 may be implemented by one or more suitable audio detection devices configured to detect an audio signal presented to a user of hearing device 102. The audio signal may include, for example, audio content (e.g., music, speech, noise, etc.) generated by one or more audio sources included in an environment of the user. Microphone 106 may be included in or communicatively coupled to hearing device 102 in any suitable manner. Output transducer 112 may be implemented by any suitable audio output device, for instance a loudspeaker of a hearing device or an output electrode of a cochlear implant system.

Inertial sensor 108 may be implemented by any suitable sensor configured to detect a motion and/or an orientation of hearing device 102 and output inertial sensor data which may include motion data and/or orientation data representative of the motion and/or orientation of hearing device 102. For example, inertial sensor 108 may include any suitable inertial measurement unit (IMU) (e.g., an accelerometer, a gyroscope, etc.). To illustrate, an accelerometer may generate motion data indicative of an acceleration of hearing device 102 in at least one of three spatial dimensions and/or orientation data indicative of an orientation of hearing device 102 relative to the direction of the gravitational force. While hearing device 102 is being worn by a user, the motion data output by inertial sensor 108 of hearing device 102 may be representative of motion by the user and/or the orientation data output by inertial sensor 108 may be representative of an orientation of the user, e.g., the head of the user. In some examples, inertial sensor 108 is included in hearing device 102. Alternatively, inertial sensor 108 may be included in a different device (e.g., a watch or a mobile device worn or carried by the user). In these alternative configurations, hearing device 102 may access inertial sensor data generated by inertial sensor 108 by being communicatively coupled to the different device.

Blood flow sensor 110 may be implemented by any suitable sensor configured to detect a property of blood flowing through vessels of the user and output blood flow data representative of the blood property. For example, blood flow sensor 110 may include an optical sensor (e.g., a photoplethysmography (PPG) sensor, which may output the blood flow data as a PPG waveform). In place of blood flow sensor 110 or in addition to blood flow sensor 110, an electrocardiogram (ECG) sensor may be implemented, which may be configured to measure an electrical activity of the heart of the user and output ECG data representative of the heart activity. In some examples, blood flow sensor 110 and/or the ECG sensor is included in hearing device 102 to position at least a portion of blood flow sensor 110 and/or the ECG sensor in sufficient contact with the user for generating blood flow data and/or ECG data. Alternatively, blood flow sensor 110 and/or the ECG sensor may be included in a different wearable device separate from hearing device 102 (e.g., a watch or a mobile device worn or carried by the user). In these alternative configurations, hearing device 102 may access blood flow data generated by blood flow sensor 110 and/or ECG data generated by the ECG sensor by being communicatively coupled to the different device.

Processing unit 104 may be implemented by one or more computing devices and/or computer resources (e.g., processors, memory devices, storage devices, etc.) as may serve a particular implementation. For example, processing unit 104 may be implemented by a mobile device, personal computer, and/or other computing device configured to be communicatively coupled (e.g., by way of a wired and/or wireless connection) to hearing device 102. As shown, processing unit 104 may include, without limitation, a memory 114 and a processor 116 selectively and communicatively coupled to one another. Memory 114 and processor 116 may each include or be implemented by computer hardware that is configured to store and/or process computer software. Various other components of computer hardware and/or software not explicitly shown in FIG. 1 may also be included within processing unit 104. In some examples, memory 114 and/or processor 116 may be distributed between multiple devices and/or multiple locations as may serve a particular implementation.

Memory 114 may store and/or otherwise maintain executable data used by processor 116 to perform any of the functionality described herein. For example, memory 114 may store instructions 118 that may be executed by processor 116. Memory 114 may be implemented by one or more memory or storage devices, including any memory or storage devices described herein, that are configured to store data in a transitory or non-transitory manner. Instructions 118 may be executed by processor 116 to cause processing unit 104 to perform any of the functionality described herein. Instructions 118 may be implemented by any suitable application, software, code, and/or other executable data instance. Additionally, memory 114 may also maintain any other data accessed, managed, used, and/or transmitted by processor 116 in a particular implementation.

Processor 116 may be implemented by one or more computer processing devices, including general purpose processors (e.g., central processing units (CPUs), graphics processing units (GPUs), microprocessors, etc.), special purpose processors (e.g., application specific integrated circuits (ASICs), field-programmable gate arrays (FPGAs), etc.), image signal processors, digital signal processors, deep neural network (DNN) acceleration processors, or the like. Using processor 116 (e.g., when processor 116 is directed to perform operations represented by instructions 118 stored in memory 114), processing unit 104 may perform various operations as described herein.

In some other implementations, various computer processing devices, which may be included in processor 116 of processing unit 104, may also be distributed between hearing device 102 and the computing device communicatively coupled to hearing device 102. E.g., hearing device 102 may include computer processing devices such as a digital signal processor and/or a control processor and/or a deep neural network (DNN) acceleration processor, and the computing device communicatively coupled to hearing device 102 may include at least an additional computing device. Further, memory 114 of processing unit 104, may also be implemented as various memory devices distributed between hearing device 102 and the computing device communicatively coupled to hearing device 102.

Figure 2:
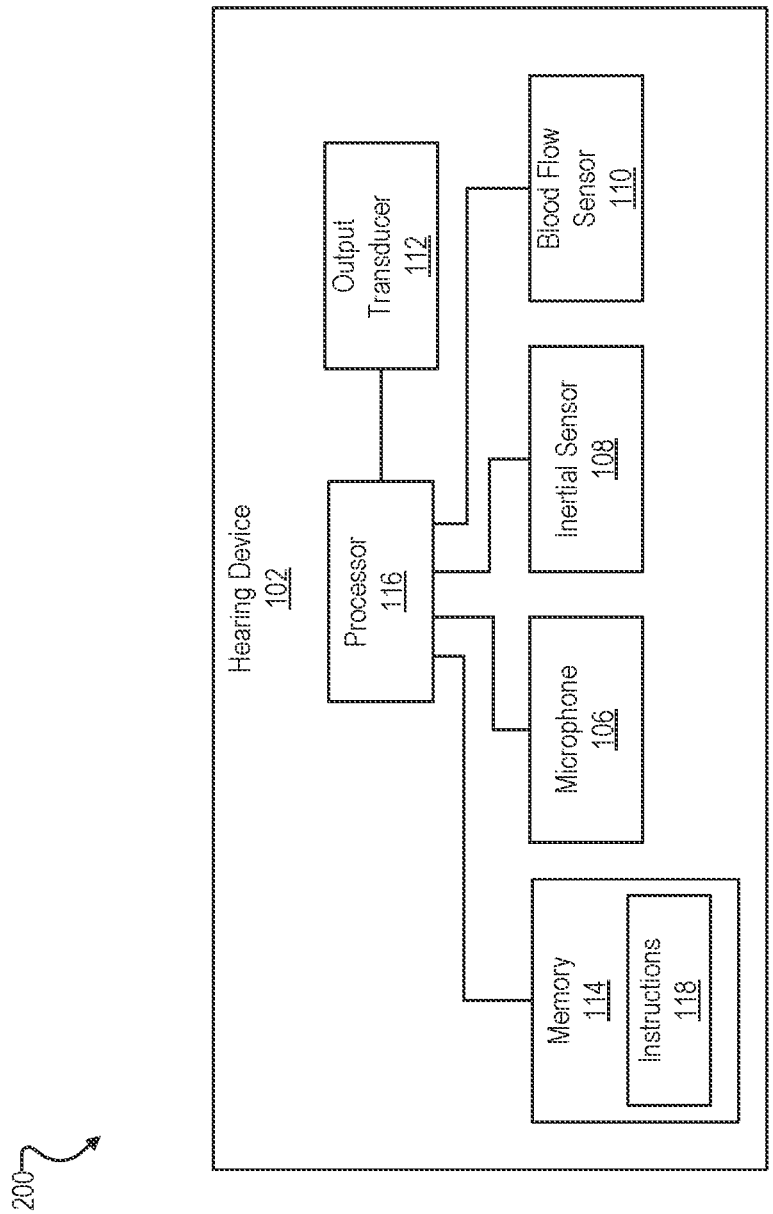
FIG. 2 shows another illustrative implementation of a hearing system.

FIG. 2 shows another illustrative implementation 200 of a hearing system configured to determine a cardiorespiratory quality index representative of a quality level of a measurement of a cardiorespiratory property of the user based on inertial sensor data received from an inertial sensor included in a hearing device configured to be worn by a user. As shown, implementation 200 is similar to implementation 100, except that implementation 200 includes processor 116 and memory 114 located within hearing device 102. Implementation 200 may include additional or alternative components as may serve a particular implementation.

Figure 3:
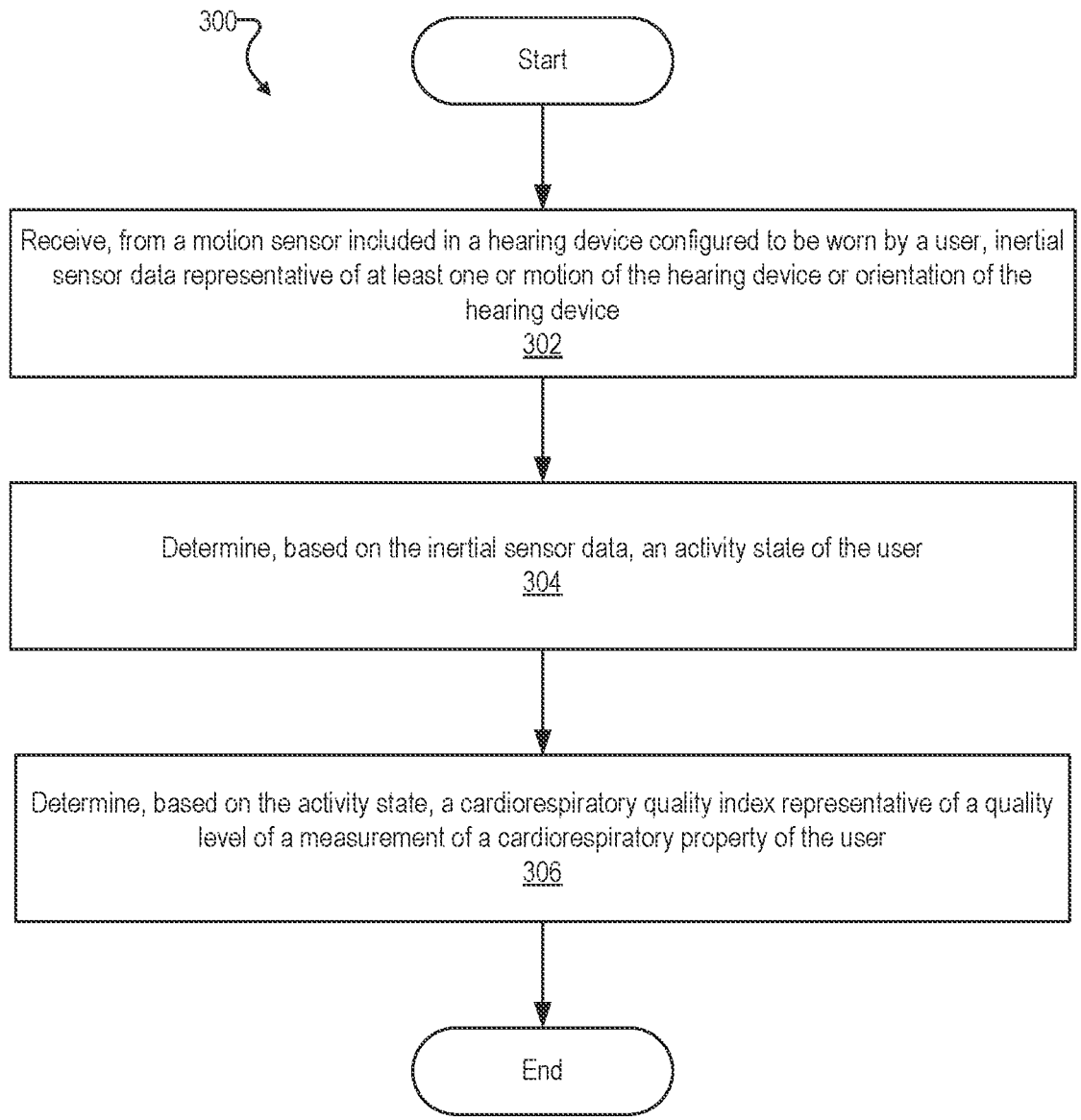
FIG. 3 shows an illustrative method of operating a hearing system.

FIG. 3 shows an illustrative method 300 that may be performed by a hearing system according to the principles described herein. While FIG. 3 illustrates exemplary operations according to one embodiment, other embodiments may omit, add to, reorder, and/or modify any of the operations shown in FIG. 3. Moreover, each of the operations depicted in FIG. 3 may be performed in any of the ways described herein.

As shown, a hearing system may, at operation 302, receive, from inertial sensor 108 included in hearing device 102 configured to be worn by a user, inertial sensor data representative of motion and/or an orientation of hearing device 102 while the user wears hearing device 102. The hearing system may, at operation 304, determine, based on the inertial sensor data, an activity state of the user. The hearing system may, at operation 306, determine, based on the activity state, a cardiorespiratory quality index representative of a quality level of a measurement of a cardiorespiratory property the user.

Figure 4:
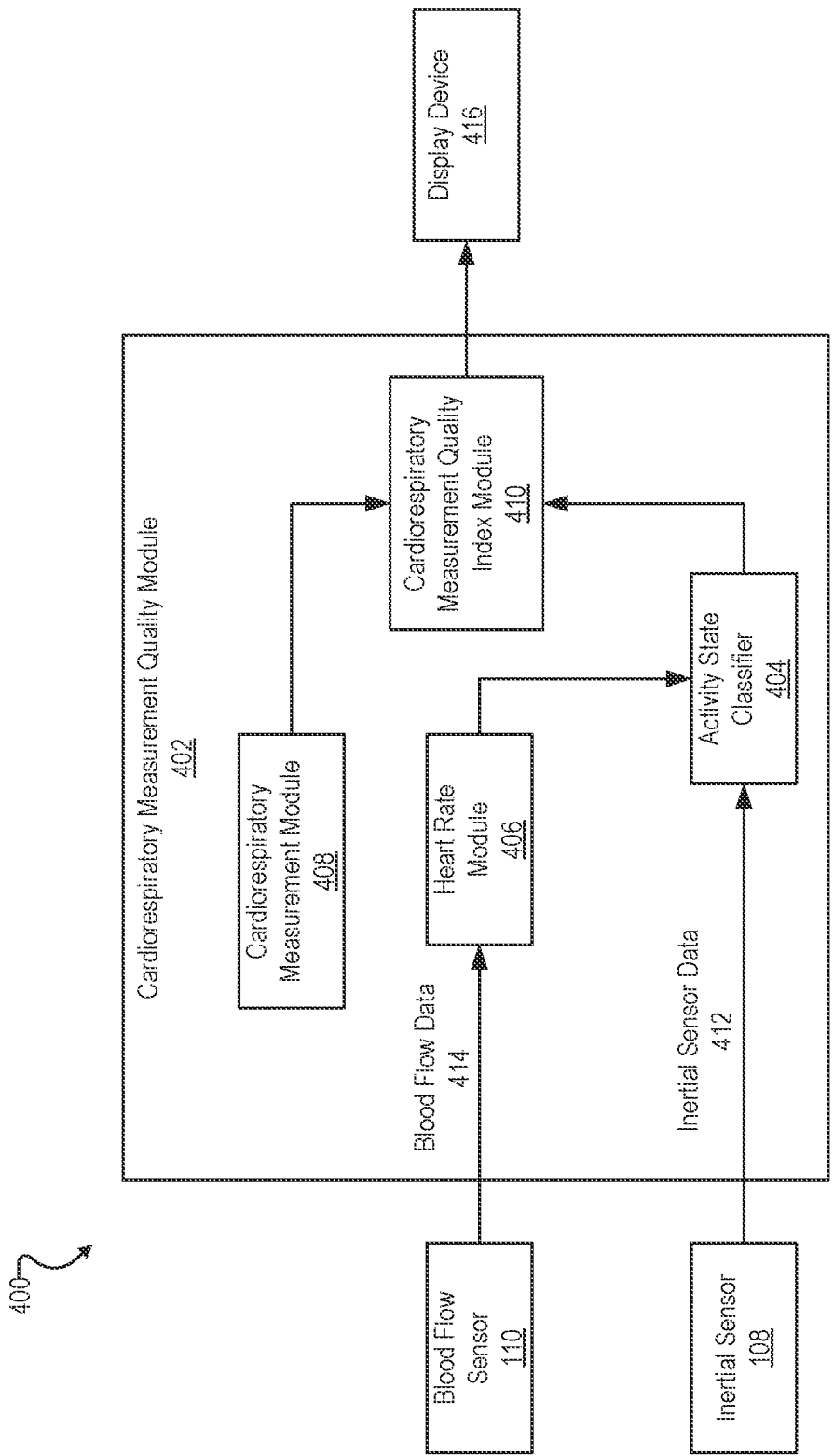
FIG. 4 shows an illustrative implementation of a cardiorespiratory measurement quality module that may be incorporated into a hearing system.

As an illustrative example, FIG. 4 shows an implementation 400 of a cardiorespiratory measurement quality module 402 that may be implemented by a hearing system according to the principles described herein and configured to determine a cardiorespiratory quality index for a measurement of a cardiorespiratory property of the user. As shown, cardiorespiratory measurement quality module 402 may include an activity state classifier 404, a heart rate module, 406, a cardiorespiratory measurement module 408, and a cardiorespiratory measurement quality index module 410. Cardiorespiratory measurement quality module 402 may include additional or alternative components as may serve a particular implementation.

Activity state classifier 404 of cardiorespiratory measurement quality module 402 may be configured to receive inertial sensor data 412 generated by inertial sensor 108 and to determine, based on the received inertial sensor data 412, an activity state of the user.

In some implementations, the activity state determined by activity state classifier 404 may include an intensity of an activity performed by the user. As an example, the intensity of the activity as performed by the user may be determined based on a frequency and/or amplitude of the inertial sensor data 412. To illustrate, motion data included in the inertial sensor data 412 may indicate the user performing an activity of low or high intensity or of various levels of the intensity depending on a frequency and/or an amplitude of the detected motions. Orientation data included in the inertial sensor data 412 may indicate the user performing an activity of low or high intensity or various degrees of intensity depending on a frequency and/or amplitude of variations in the detected orientation. As another example, the intensity of the activity as performed by the user may be determined based on a duration in which the inertial sensor data 412 lies within a defined range of frequency and/or amplitude, e.g. below or above a frequency and/or amplitude threshold or between various levels of frequency and/or amplitude thresholds. To illustrate, motion data and/or orientation data included in the inertial sensor data 412 may indicate the user performing an activity of low or high intensity or of various levels of the intensity depending on a duration of the detected motions and/or variations of the detected orientations within a specific frequency and/or amplitude range. E.g., the longer the duration of a rather large frequency and/or amplitude of the inertial sensor data 412, the larger the intensity of the activity may be determined.

In some implementations, the determined activity state may include a level of stress (e.g., physical or mental stress) of the user. As an example of physical stress, inertial sensor data 412 indicating a high level of intensity of the activity performed by the user and/or having a high frequency and/or amplitude may indicate a high level of physical stress to the user. Such high levels of physical stress may be representative of the user performing a physical activity. Alternatively, inertial sensor data 412 indicating a low level of intensity of the activity performed by the user and/or having a low frequency and/or amplitude may indicate a low level of physical stress to the user, which may be representative of the user not performing a physical activity. In some instances, the determined level of stress may include a duration of the stress and/or a period of recovery time after the stress has been detected based on motion data 412.

In some implementations, the activity state determined by activity state classifier 404 may include a type of activity that the user is performing. To this end, activity state classifier 404 may be configured to classify inertial sensor data 412 with regard to at least one activity type or a plurality of different activity types. For example, activity state classifier 404 may be configured to determine whether inertial sensor data 412 matches a motion pattern and/or a change of orientation pattern associated with a respective activity type. E.g., one or more types of the activity may include at least one of a sedentary activity, light household work, walking, running, swimming, bicycling, driving a car, dancing, chewing, talking, or the like. In some instances, the type of the activity may be associated with a high level of stress to the user and/or a high intensity activity (e.g., running, jogging, dancing, etc.), a moderate level of stress to the user and/or a moderate intensity activity (e.g., walking, swimming, driving a car, talking, chewing, etc.), and/or a low level of stress to the user and/or a low intensity activity (e.g., sitting, standing, laying down, etc.).

In some implementations, the activity state determined by activity state classifier 404 may include a posture of the user. For example, the posture of the user may be determined based on orientation data included in the inertial sensor data 412, e.g. an orientation relative to a reference orientation such as gravity and/or the earth's magnetic field, and/or based on motion data included in the inertial sensor data 412, e.g. by identifying a momentary posture based on the user's motion changing the posture from a previous posture. For instance, the posture may include a body posture, which may include a horizontal and vertical body position and/or various degrees in between, e.g. one or more of an upright body position, a sedentary body position, a reclining body position, and a recumbent body position, and/or a head posture, e.g. a tilting of the head to the left or right and/or up or down. In some instances, the posture may be employed as a classification of a low intensity activity (e.g., sitting, standing, laying down, etc.), e.g. to increase the number of gradation levels of the activity state. In some other instances, the posture can be a separate quantity included in the activity state, e.g. to determine the cardiorespiratory quality index based on the posture and at least another quantity included in the activity state independent from one another.

Activity state classifier 404 may further be configured to determine a change in the activity state. For example, activity state classifier may be configured to determine a change in the level of stress to the user, a change in the intensity and/or type of activity that the user is performing, a change in posture and/or a change in motion and/or orientation of the user.

In some implementations, activity state classifier 404 may be configured to receive data representative of a heart rate of the user to determine the activity state based the heart rate of the user. For example, heart rate module 406 of cardiorespiratory measurement quality module 402 may receive blood flow data 414 from blood flow sensor 110 and/or ECG data from an ECG sensor. Heart rate module 406 may be configured to process blood flow data 414 and/or the ECG data to provide a heart rate of the user to activity state classifier 404. Accordingly, activity state classifier 404 may determine the activity state of the user based on the heart rate of the user. For example, a high heart rate may indicate a high level of stress to the user. Alternatively, a low heart rate may indicate a low level of stress to the user. The activity state may be determined by activity state classifier 404 based on the heart rate of the user in addition to inertial sensor data 412, e.g. to determine the activity state with improved accuracy. To illustrate, a level of stress may be determined at a higher accuracy when taking into account the heart rate of the user, which can be indicative of both physical and mental stress, whereas inertial sensor data 412 may be mostly representative of physical stress. Further, additional evaluation of the heart rate of the user can also facilitate identifying an intensity and/or type of an activity performed by the user based on the inertial sensor data 412.

In some implementations, activity state classifier 404 may be configured to receive an audio signal detected by microphone 106 of hearing device 102 to further determine the activity state of the user based the received audio signal, e.g. in addition to inertial sensor data 412 and/or the heart rate of the user. For example, the audio signal may include audio content (e.g., music, speech, noise, etc.) generated by one or more audio sources included in an environment of the user. Such audio signals may allow activity state classifier 404 to determine a type of activity that the user is performing. For example, activity state classifier 404 may determine that a user is eating and/or drinking when the audio signal includes audio content representative of the user eating and/or drinking (e.g., chewing, swallowing, a sound of a coffee machine, etc.). Additionally or alternatively, the level of mental stress of the user may be determined based on the received audio signal. For example, the audio signal may include audio content having loud and/or stressful sounds (e.g., yelling, loud music, action in a television scene, etc.) that may indicate a high level of mental stress to the user. Alternatively, the audio signal may include audio content having soft and/or soothing sounds (e.g., soft music, meditation, etc.) that may indicate a low level of mental stress to the user.

In some implementations, the audio signal may further include an own voice content representative of an activity of the user's own voice. E.g., cardiorespiratory measurement quality module 402 may comprise a voice activity detector (VAD) configured to identify the user's own voice in the audio signal detected by microphone 106 and to provide own voice data representative of the user's own voice to activity state classifier 404. Activity state classifier 404 may be configured to determine the activity state of the user based on the own voice content in the audio signal, e.g. based on the own voice data. To illustrate, the user yelling and/or speaking fast may indicate a high level of mental stress to the user. The user being quiet and/or talking with a calm voice may indicate a low level of mental stress to the user. The own voice content may also be employed to improve identifying an intensity and/or type of activity performed by the user.

In some implementations, the audio signal may further include a voice input from the user. This may allow the user to vocalize a status and/or activity that the user is performing. For example, the user may vocalize when the user is taking medication related to the cardiorespiratory property, e.g. blood pressure medication. In some implementations, the hearing system may be configured to request voice input from the user regarding the activity state of the user (e.g., by a mobile device or other user interface). Activity state classifier 404 may further be configured to determine a level of mental stress of the user based on the voice input received from the user (e.g., by voice analysis, vocal biomarkers, etc.).

In some implementations, activity state classifier 404 may be configured to receive data representative of a respiratory rate of the user to further determine the activity state of the user based on the respiratory rate, e.g. in addition to inertial sensor data 412 and/or the heart rate of the user and/or the audio signal detected by microphone 106. For example, a respiratory rate of the user may be determined by heart rate module 406 (or by an additional respiratory rate module) based on blood flow data 414 generated by blood flow sensor 110. Alternatively, a respiratory rate of the user may be detected by a separate device (e.g., a respirator) communicatively coupled with the hearing system. To illustrate, the user having an increased respiration rate may indicate a high level of physical and/or mental stress to the user. The user having a regular and/or average respiration rate may indicate a low level of physical and/or mental stress to the user. The respiratory rate may also be employed to improve identifying an intensity and/or type of activity performed by the user.

In some implementations, activity state classifier 404 may be configured to receive data representative of a heart rate variability of the user to further determine the activity state of the user based on the heart rate variability, e.g. in addition to inertial sensor data 412 and/or the heart rate of the user and/or the audio signal detected by microphone 106 and/or the respiratory rate. For example, a heart rate variability of the user may be determined by heart rate module 406 (or by an additional heart rate variability module) based on blood flow data 414 generated by blood flow sensor 110 and/or based on ECG data provided by an ECG sensor and/or by a separate device communicatively coupled with the hearing system. E.g., the heart rate variability may also be employed as an indicator of a stress level to the user and/or to improve identifying an intensity and/or type of activity performed by the user.

In some implementations, activity state classifier 404 may be configured to receive data representative of a body temperature of the user to further determine the activity state of the user based on the body temperature, e.g. in addition to inertial sensor data 412 and/or the heart rate of the user and/or the audio signal detected by microphone 106 and/or the respiratory rate and/or the heart rate variability. For example, a body temperature of the user may be determined by a temperature sensor included in hearing device 102 which may provide temperature data to heart rate module 406 (or an additional body temperature module). Alternatively, a body temperature of the user may be detected by a separate device (e.g., a thermal sensor) communicatively coupled with the hearing system.

Still other suitable configurations and/or methods may be used by activity state classifier 404 to determine an activity state of the user. For example, activity state classifier 404 may be configured to receive data representative of a location of the user (e.g., by a global positioning system (GPS)) and/or a time of day (e.g., by a clock) for determining the activity state of the user. In some implementations, activity state classifier 404 may be configured to learn various activity states of the user over time based on previous data received by activity state classifier 404 while in the various activity states.

Cardiorespiratory measurement quality index module 410 may be configured to receive data representative of the determined activity state of the user from activity state classifier 404. Cardiorespiratory measurement quality index module 410 may be further configured to determine, based on the activity state, a cardiorespiratory quality index representative of a quality level of a measurement of a cardiorespiratory property of the user in the determined activity state. For example, cardiorespiratory measurement quality index module 410 may be configured to receive a measurement of the cardiorespiratory property of the user from cardiorespiratory measurement module 408. In some implementations, cardiorespiratory measurement module 408 may determine a measurement of the cardiorespiratory property of the user based on blood flow data 414 generated by blood flow sensor 110 and/or ECG data generated by an ECG sensor. E.g., a blood pressure and/or a respiration rate and/or a heart rate variability may be measured by the cardiorespiratory measurement module 408 based on blood flow data 414 and/or ECG data. A blood analyte level and/or a capillary oxygen saturation may be measured based on blood flow data 414. Additionally or alternatively, cardiorespiratory measurement module 408 may be configured to receive a measurement of the cardiorespiratory property of the user from a different wearable device (e.g., a blood pressure cuff, a watch, or a mobile device worn or carried by the user). In these alternative configurations, cardiorespiratory measurement module 408 may access measurements of the cardiorespiratory property being communicatively coupled to the different device.

Cardiorespiratory measurement quality index module 410 may determine the cardiorespiratory quality index for a measurement of the cardiorespiratory property taken in the determined activity state by activity state classifier 404. For example, cardiorespiratory measurement quality index module 410 may be configured to decrease the cardiorespiratory quality index when the activity state indicates an intensity and/or type of the activity and/or level of stress and/or posture and/or change thereof representative of a lower measurement quality. E.g., in the case of a blood pressure measurement, the cardiorespiratory quality index may be a blood pressure quality index which may be reduced when the activity state includes a high level of stress and/or a posture of the user different from a sedentary body position and/or a high intensity of the activity and/or a high level of motion of the user and/or a large level of changes thereof. Alternatively, cardiorespiratory measurement quality index module 410 may be configured to increase the cardiorespiratory quality index when the activity state indicates an intensity and/or type of the activity and/or level of stress and/or posture and/or change thereof representative of a lower measurement quality. E.g., in the case of a blood pressure measurement, the blood pressure quality index may be increased when the activity state includes a low level of stress and/or a posture of the user in a sedentary body position and/or a low intensity of the activity and/or a low level of motion of the user and/or a small level of changes thereof. The cardiorespiratory quality index may be represented by any suitable metric, such as a discrete value (e.g., a percentage, a level, a range, a probability value, etc.) representative of a quality level of the measurement of the cardiorespiratory property taken in the determined activity state.

Cardiorespiratory measurement quality index module 410 may be configured to determine the cardiorespiratory quality index for a measurement of one or more cardiorespiratory properties. For example, a first cardiorespiratory quality index may be determined for a measurement of a first cardiorespiratory property, and a second cardiorespiratory quality index may be determined for a measurement of a second cardiorespiratory property different from the first cardiorespiratory property. In some instances, when determining the cardiorespiratory quality index for a respective measurement of different cardiorespiratory properties, the activity state may be evaluated differently and/or independently for the respective cardiorespiratory quality index, e.g. depending on the respective cardiorespiratory property. For example, when determining the first cardiorespiratory quality index associated with the first cardiorespiratory property, the activity state may be taken into account depending on the first cardiorespiratory property, and, and when determining the second cardiorespiratory quality index associated with the second cardiorespiratory property, the activity state may be taken into account depending on the second cardiorespiratory property. In this way, different dependencies of the quality level of a measurement of different cardiorespiratory properties on the activity state can be taken into account.

To illustrate, when the measurement of the cardiorespiratory property is a blood pressure measurement, the quality level may depend to a rather large extent on a posture of the user and/or a change of the posture, among other factors such as a level of stress to the user and/or a resting period before the measurement. When the measurement of the cardiorespiratory property is a measurement of at least one of a respiratory rate, a heart rate variability, a blood analyte level, and a capillary oxygen saturation (SpO2), the quality level may depend to a lesser extent on the posture and/or change of posture, but may mostly depend on other factors such as the stress level and/or the intensity and/or type of an activity performed by the user and/or a level and/or duration of motion of the user, wherein the dependency may vary for the respective cardiorespiratory property which is to be measured. When determining the cardiorespiratory quality index for the blood pressure measurement (e.g., as a blood pressure quality index), the posture of the user and/or other activity indicators represented by the activity state may thus be taken into account differently as compared to when determining the cardiorespiratory quality index for the measurement of another cardiorespiratory property (e.g., as a respiratory rate quality index, a heart rate variability quality index, a blood analyte level quality index, or an SpO2 quality index). As another example, a measurement of a heart rate variability may have a highest quality during a resting state of the user. A measurement of a capillary oxygen saturation may substantially not vary when the user is resting or performing activities of a light intensity such that the measurement quality may be estimated as equal in both cases. Thus, when determining a heart rate variability quality index and a SpO2 quality index, the intensity and/or type of the activity performed by the user and/or other activity indicators represented by the activity state may be taken into account differently.

Cardiorespiratory measurement quality index module 410 may further be configured to transmit and/or output the cardiorespiratory quality index to a display device 416 (e.g., a watch, mobile device, etc.) to display the cardiorespiratory quality index to the user. In some implementations, cardiorespiratory measurement quality index module 410 may be configured to associate the cardiorespiratory quality index with the measurement of the cardiorespiratory property and transmit and/or output the cardiorespiratory quality index in combination with the measurement of the cardiorespiratory property to display device 416, e.g. in combination with measurement data representative of the measurement. In some implementations, display device 416 may be configured to display a plot of the cardiorespiratory quality index and/or measurement of the cardiorespiratory property over time.

In some implementations, cardiorespiratory measurement quality module 402 may perform, based on the cardiorespiratory quality index, an operation with respect to hearing device 102. For example, when the cardiorespiratory quality index is less than a threshold, cardiorespiratory measurement quality module 402 may abstain from taking a measurement of the cardiorespiratory property of the user. Additionally or alternatively, when the cardiorespiratory quality index is less than a threshold, cardiorespiratory measurement quality module 402 may disable sensor 110 and/or an ECG sensor and/or another device configured to measure the cardiorespiratory property of the user. E.g., the hearing system may abstain from taking a blood pressure measurement and/or disable the device generating the blood pressure measurement during unsuitable conditions such as too much movement and/or stress and/or an unsuitable posture of the user. Further, cardiorespiratory measurement quality module 402 may also interrupt and/or (partially) invalidate such measurements if the quality index drops below a threshold during such a measurement. Cardiorespiratory measurement quality module 402 may also change a configuration of the blood flow sensor 110 and/or an ECG sensor when a low-quality index is indicated. For instance, when blood flow sensor 110 is implemented as an optical sensor, such a configuration change may increase, e.g., an illumination of an LED included in blood flow sensor 110 and/or change a wavelength of the illumination, and/or or increase a sensitivity of a photodetector included in blood flow sensor 110. Cardiorespiratory measurement quality module 402 may also initiate a recording of blood flow data 414 and/or of ECG data when the quality index exceeds a threshold, e.g. for a predetermined time interval. For instance, the recording may comprise storing blood flow data 414 and/or the ECG data in a memory, e.g. in memory 114, which may comprise a volatile and/or a non-volatile memory. The recorded data may be retrieved and evaluated, e.g. by cardiorespiratory measurement module 408, at a later time. To this end, cardiorespiratory measurement module 408 may be included in hearing device 102 or in a further device. If in a further device, the recorded data may be retrieved by transferring the recorded data, e.g. from a memory in which the recorded data is stored, via a communication interface to cardiorespiratory measurement module 408 at a suitable time, e.g. during or after the recording of the of blood flow data 414 and/or the ECG data. Still other suitable configurations for cardiorespiratory measurement quality module 402 may be used.

Figure 5:
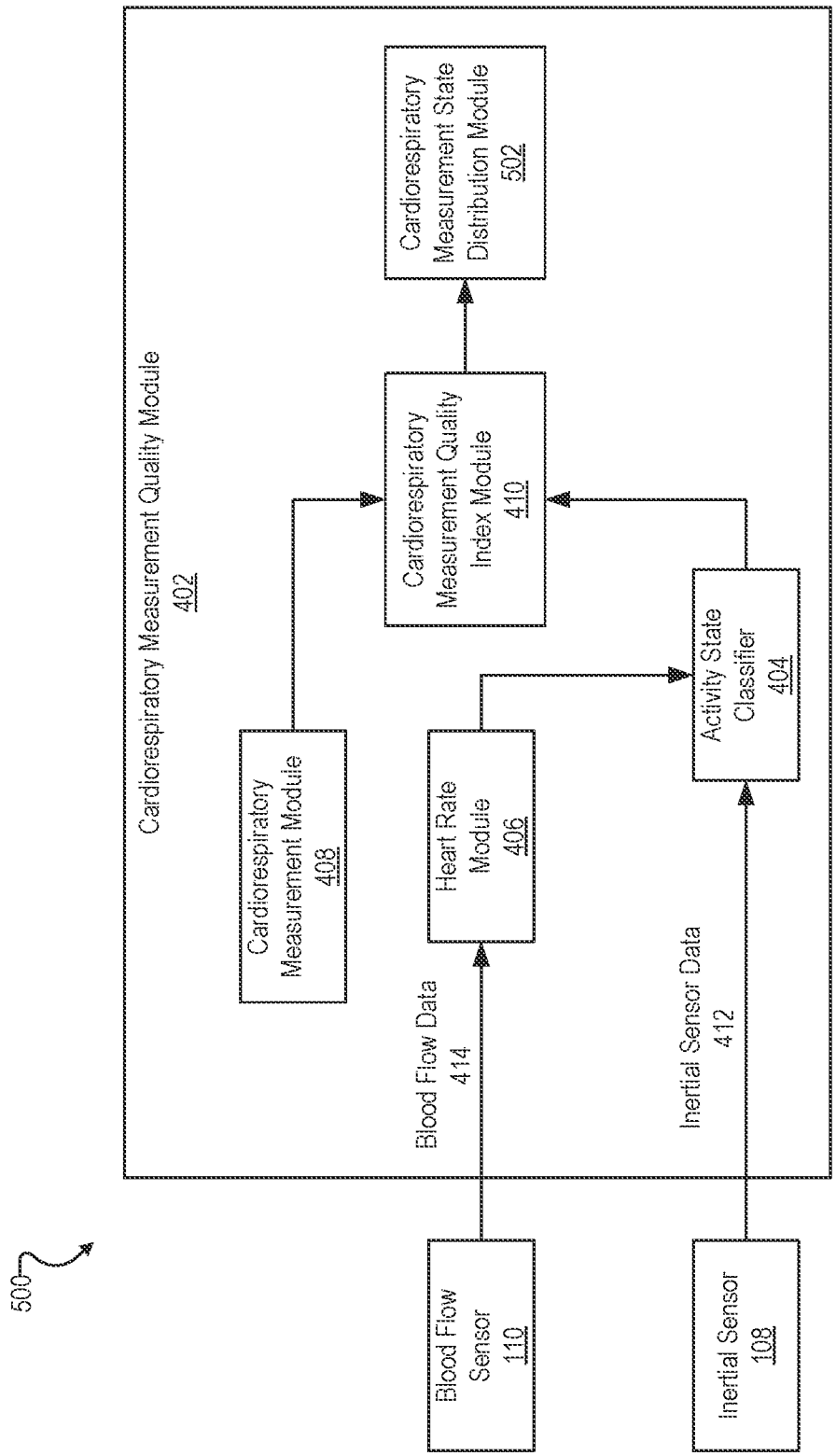
FIG. 5 shows another illustrative implementation of a cardiorespiratory measurement quality module that may be incorporated into a hearing system.

As an illustrative example, FIG. 5 shows another implementation 500 of cardiorespiratory measurement quality module 402 that further includes a cardiorespiratory measurement state distribution module 502. Cardiorespiratory measurement state distribution module 502 may be configured to receive the cardiorespiratory quality index from cardiorespiratory measurement quality index module 410. Cardiorespiratory measurement state distribution module 502 may be further configured to store the cardiorespiratory quality index and/or the measurement of the cardiorespiratory property in a cardiorespiratory measurement state distribution representative of a curve of measurements of the cardiorespiratory property. In some implementations, cardiorespiratory measurement state distribution module 502 may be configured to cumulatively store the received data by combining the received data for multiple activity states in a single cardiorespiratory measurement state distribution. Alternatively, cardiorespiratory measurement state distribution module 502 may be configured to separately store the received data in a separate cardiorespiratory measurement state distribution for each determined activity state. Such stored cardiorespiratory measurement state distributions may be accessed by cardiorespiratory measurement quality index module 410 for determining the cardiorespiratory quality index. For example, the cardiorespiratory measurement state distributions may be representative of the likelihood of occurrence of the measurement of the cardiorespiratory property in the determined activity state.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM") or static random access memory ("SRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read. Instructions, as stored in non-volatile memory, are usually first transferred to volatile memory for execution by the processor.

Figure 6:
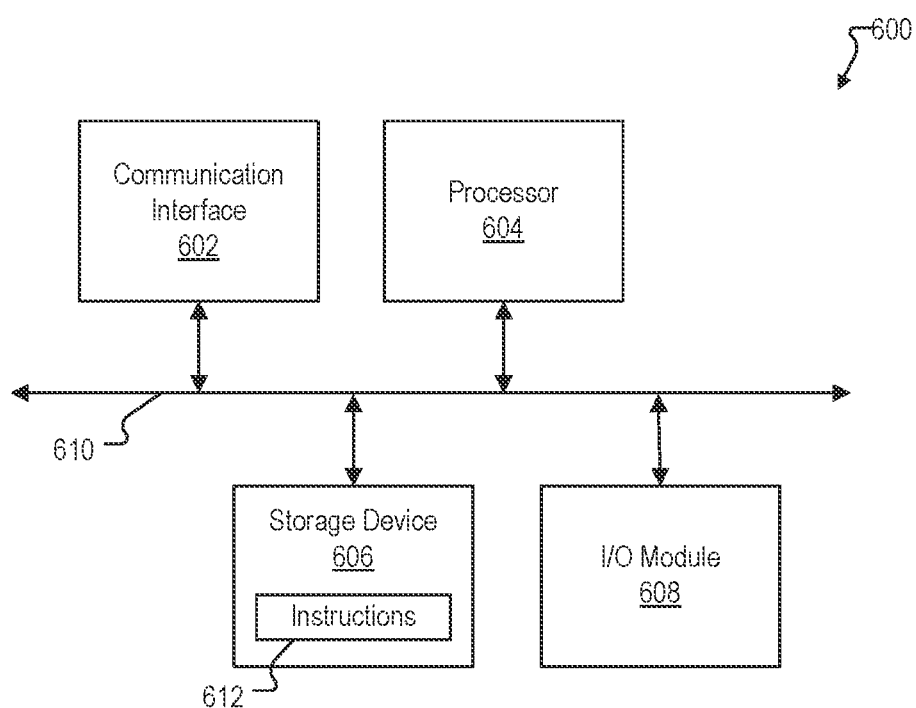
FIG. 6 shows an illustrative computing system according to the principles described herein.

FIG. 6 shows an illustrative computing device 600 that may be specifically configured to perform one or more of the processes described herein. Any of the systems, computing devices, and/or other components described herein may be implemented by computing device 600.

As shown in FIG. 6, computing device 600 may include a communication interface 602, a processor 604, a storage device 606, and an input/output ("I/O") module 608 communicatively connected one to another via a communication infrastructure 610. While an illustrative computing device 600 is shown in FIG. 6, the components illustrated in FIG. 6 are not intended to be limiting. Additional or alternative components may be used in other embodiments. Components of computing device 600 shown in FIG. 6 will now be described in additional detail.

Communication interface 602 may be configured to communicate with one or more computing devices. Examples of communication interface 602 include, without limitation, a wired network interface (such as a network interface card), a wireless network interface (such as a wireless network interface card), a modem, an audio/video connection, a radio transceiver, and any other suitable interface.

Processor 604 generally represents any type or form of processing unit capable of processing data and/or interpreting, executing, and/or directing execution of one or more of the instructions, processes, and/or operations described herein. Processor 604 may perform operations by executing computer-executable instructions 612 (e.g., an application, software, code, and/or other executable data instance) stored in storage device 606. Processor 604 may comprise one or multiple processing devices, e.g. processing cores, with equal and/or different architecture, which may utilize separate ("private") memory and/or share common memory, e.g. implemented in storage device 606.

Storage device 606 may include one or more data storage media, devices, or configurations and may employ any type, form, and combination of data storage media and/or device. For example, storage device 606 may include, but is not limited to, any combination of the non-volatile media and/or volatile media described herein. Electronic data, including data described herein, may be temporarily and/or permanently stored in storage device 606. For example, data representative of computer-executable instructions 612 configured to direct processor 604 to perform any of the operations described herein may be stored within storage device 606. In some examples, data may be arranged in one or more databases residing within storage device 606.

I/O module 608 may include one or more I/O modules configured to receive user input and provide user output. I/O module 608 may include any hardware, firmware, software, or combination thereof supportive of input and output capabilities. For example, I/O module 608 may include hardware and/or software for capturing user input, including, but not limited to, a keyboard or keypad, a touchscreen component (e.g., touchscreen display), a receiver (e.g., an RF or infrared receiver), inertial and/or motion sensors, a touchpad, and/or one or more input buttons.

I/O module 608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 608 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    a hearing device configured to be worn by a user, the hearing device comprising:
        an inertial sensor configured to detect at least one of motion of the hearing device or an orientation of the hearing device;
        a microphone configured to detect an audio signal presented to the user; and
        an output transducer configured to output the audio signal detected by the microphone to the user;
    a memory storing instructions; and
    a processor communicatively coupled to the memory and configured to execute the instructions to:
        receive, from the inertial sensor, inertial sensor data representative of the at least one of motion of the hearing device or orientation of the hearing device;
        determine, based on the inertial sensor data, an activity state of the user; and
        determine, based on the activity state, a cardiorespiratory quality index representative of a quality level of a measurement of a cardiorespiratory property of the user.

2. The system of claim 1, wherein the activity state is representative of at least one of: an intensity of an activity performed by the user; a type of an activity performed by the user; a level of stress to the user; and a posture of the user.

3. The system of claim 1, wherein the cardiorespiratory property includes one or more of the following: a blood pressure, a respiratory rate, a heart rate variability, a blood analyte level, and a capillary oxygen saturation.

4. The system of claim 1, wherein the processor is further configured to execute the instructions to transmit the cardiorespiratory quality index to a display device configured to provide a display of the cardiorespiratory quality index to the user.

5. The system of claim 1, wherein the processor is further configured to receive condition data including at least one of blood flow data of the user from a blood flow sensor in contact with the user or electrocardiogram data of the user from an electrocardiogram sensor in contact with the user.

6. The system of claim 5, wherein the processor is further configured to determine, based on the condition data, a heart rate measurement of the user, wherein the determination of the activity state of the user is further based on the heart rate measurement.

7. The system of claim 6, wherein the processor is further configured to:
determine, based on the condition data, the measurement of the cardiorespiratory property of the user, wherein the cardiorespiratory property is different from the heart rate measurement; and
associate the cardiorespiratory quality index with the measurement of the cardiorespiratory property.

8. The system of claim 7, wherein the processor is further configured to execute the instructions to transmit the cardiorespiratory quality index to a display device configured to provide a display of the cardiorespiratory quality index in combination with the measurement of the cardiorespiratory property to the user.

9. The system of claim 5, wherein at least one of the blood flow sensor or the electrocardiogram sensor is included in the hearing device.

10. The system of claim 5, wherein at least one of the blood flow sensor or the electrocardiogram sensor is included in a wearable device separate from the hearing device.

11. The system of claim 1, wherein the measurement of the cardiorespiratory property is performed by the hearing device.

12. The system of claim 1, wherein the measurement of the cardiorespiratory property is performed by a wearable device separate from the system.

13. The system of claim 1, wherein the processor is further configured to execute the instructions to store the measurement of the cardiorespiratory property in a cardiorespiratory measurement state distribution representative of a curve of measurements of the cardiorespiratory property in the activity state.

14. The system of claim 1, wherein the processor is further configured to execute the instructions to perform, based on the cardiorespiratory quality index, an operation with respect to the hearing device.

15. The system of claim 14, wherein, when the cardiorespiratory quality index is less than a threshold, the operation comprises at least one of abstaining from taking a measurement of the cardiorespiratory property of the user; interrupting the measurement; invalidating at least part of measurement data obtained from the measurement; changing a configuration of a select one or both of a blood flow sensor or an electrocardiogram sensor in contact with the user; and disabling a select one or both of the blood flow sensor or the electrocardiogram sensor in contact with the user.

16. The system of claim 14, wherein, when the cardiorespiratory quality index exceeds a threshold, the operation comprises at least one of taking a measurement of the cardiorespiratory property of the user; enabling a select one or both of a blood flow sensor or an electrocardiogram sensor in contact with the user; and initiating a recording of data generated by a select one or both of a blood flow sensor or an electrocardiogram sensor in contact with the user.

17. The system of claim 1, wherein the processor is further configured to execute the instructions to:
receive, from the hearing device, the audio signal detected by the microphone of the hearing device;
wherein the determining of the activity state of the user is further based on the audio signal.

18. A system comprising:
a hearing device configured to be worn by a user comprising:
an inertial sensor;
a microphone configured to detect an audio signal presented to the user; and
an output transducer configured to output the audio signal detected by the microphone to the user; and
a processing unit communicatively coupled to the inertial sensor and configured to:
receive, from the inertial sensor, inertial sensor data representative of at least one of a motion of the hearing device or an orientation of the hearing device;
determine, based on the inertial sensor data, an activity state of the user; and
determine, based on the activity state, a cardiorespiratory quality index representative of a quality level of a measurement of a cardiorespiratory property of the user.

19. The system of claim 18, wherein the processing unit is implemented by a computing device separate from the hearing device.

20. The system of claim 18, wherein the processing unit is located within the hearing device.

21. A method comprising:
receiving, from a hearing device configured to be worn by a user and comprising an inertial sensor, a microphone configured to detect an audio signal presented to the user, and an output transducer configured to output the audio signal detected by the microphone to the user, inertial sensor data representative of at least one of a motion of the hearing device or an orientation of the hearing device;
determining, based on the inertial sensor data, an activity state of the user; and
determining, based on the activity state, a cardiorespiratory quality index representative of a quality level of a measurement of a cardiorespiratory property of the user.

* * * * *